United States Patent [19]

Nakamura et al.

[11] Patent Number: 5,952,211
[45] Date of Patent: Sep. 14, 1999

[54] METHOD FOR PRODUCING ACTIVE HUMAN ALANINE AMINOTRANSFERASE

[76] Inventors: Atsuo Nakamura, 580-103, Hirakata-cho, Nagahama, Shiga-ken, Japan; Toshio Tanaka, 580-204, Hirakata-cho, Nagahama, Shiga-ken, Japan; Yushi Matuo, 6-16-15, Senriyamanishi, Suita, Osaka-fu, Japan; Sumio Tanase, 13-34, Higashimachi-kitajutaku, 4-18, Higashi-machi, Kumamoto, Kumamoto-ken, Japan; Masahiko Funatsu, Tsuinkuru-tounomoto A202, 69, Kanokogi-machi, Kumamoto, Kumamoto-ken, Japan; Akira Eto, 68, Jinnai, Tatsuda-machi, Kumamoto, Kumamoto-ken, Japan

[21] Appl. No.: 08/941,647

[22] Filed: Sep. 30, 1997

Related U.S. Application Data

[63] Continuation of application No. 08/533,717, Sep. 26, 1995, abandoned.

[30] Foreign Application Priority Data

Oct. 7, 1994 [JP] Japan ................................. 6-268119

[51] Int. Cl.⁶ .............................. C12N 9/10; C07H 21/04
[52] U.S. Cl. ................. 435/193; 435/252.3; 435/252.33; 435/320.1; 536/23.1; 536/23.2; 536/23.5
[58] Field of Search ..................... 435/193, 240, 435/252.3, 252.33, 252–8, 320.1; 536/23.1, 23.2, 23.5

[56] References Cited

U.S. PATENT DOCUMENTS

| 5,240,831 | 8/1993 | Barnes .................................. 435/69.1 |
| 5,420,027 | 5/1995 | Fisher et al. ............................ 435/189 |

FOREIGN PATENT DOCUMENTS

| 5-068548 | 3/1993 | Japan . |

OTHER PUBLICATIONS

Keiichi Itakura, Tadaaki Hirose, Roberto Crea, Arthur D. Riggs, Herbert L. Heyneker, Francisco Bolivar and Herbert W. Boyer. "Expression in *Escherichia coli* of a Chemically Synthesized Gene for the Hormone Somatostatin". *Science*, vol. 198, pp. 1056–1063. 1977.

Hiuga Saito and Kin–Ichiro Miura. "Preparation of Transforming Deoxyribonucleic Acid by Phenol Treatment". *Biochimica Et Biophysica Acta*, vol. 72, pp. 619–629. 1963.

Achilles Dugaiczyk, Herbert W. Boyer and Howard M. Goodman. "Ligation of Ecori Endonuclease–Generated DNA Fragments Into Linear and Circular Structures". *J. Mol. Biol.*, vol. 96, pp. 171–184. 1975.

C. T. Chung, Suzanne L. Niemela and Roger H. Miller. One–Step Preparation of Competent *Escherichia coli*: Transformation and Storage of Bacterial Cells in the Same Solution. *Proc. Natl. Acad. Sci. USA*, vol. 86, pp. 2172–2175. 1989.

H.C. Birnboim and J. Doly. "A Rapid Alkaline Extraction Procedure for Screening Recombinant Plasmid DNA", *Nucleic Acids Research*, vol. 7, No. 6, pp. 1513–1523. 1979.

U.K. Laemmli. "Cleavage of Structural Proteins During the Assembly of the Head of Bacteriophage T4". *Nature*, vol. 227, pp. 680–685. 1970.

Devlin et al. "Alteration of amino–terminal codons of human granulocyte–colony–stimulating factor increases expression level and allows efficient . . . " Gene 65, 13–22, 1988.

Grosjean et al. "Preferential codon usage in prokaryotic genes: the optimal codon–anticodon interaction energy and selective codon usage in efficiently expressed genes" Gene 18, 199–209, 1982.

Sambrook et al. "Molecular Cloning: A laboratory Manual" 2nd Ed. Cold Spring Harbor Lab. Press, 1989.

*Primary Examiner*—Robert A. Wax
*Assistant Examiner*—Nashaat T. Nashed

[57] ABSTRACT

The invention relates to a mutated human ALT (alanine aminotransferase) gene improving the DNA sequence encoding the N-terminal region of human ALT, without causing amino acid substitution, while, at the same time, adding restriction endonuclease sites to the upstream and downstream sites of the gene. By cultivation of *E. coli* transformant carrying a recombinant plasmid, which was constructed by ligation of the mutated human ALT gene into a vector, an active human ALT can be produced efficiently.

9 Claims, 5 Drawing Sheets

```
   1  AGCGCCCAAT ACGCAAACCG CCTCTCCCCG CGCGTTGGCC GATTCATTAA TGCAGCTGGC
  61  ACGACAGGTT TCCCGACTGG AAAGCGGGCA GTGAGCGCAA CGCAATTAAT GTGAGTTAGC
 121  TCACTCATTA GGCACCCCAG GCTTTACACT TTATGCTTCC GGCTCGTATG TTGTGTGGAA
 181  TTGTGAGCGG ATAACAATTT CACACAGGAA ACAGCTATGA CCATGATTAC GCCAAGCTCT
```
                                                          E. coli K12 TRP PROMOTER

```
 241  AATACGACTC ACTATAGGGA AAGCTT  CCCTGTTGACAATTAATCATCGAACTAGTTAAC
                                HindIII 300              AGTACGCAAGTTCACGTAAAAAGGGTA   GAATTCGAGCTCGGTACCCGGGGGATCCTCTAGA
                                                  EcoRI                 BamHI
 361  GTCGACCTGCAGGTCGAAATTC  ACTGGCCG TCGTTTTACA ACGTCGTGAC TGGGAAAACC
              PstI
 421  CTGGCGTTAC CCAACTTAAT CGCCTTGCAG CACATCCCCC TTTCGCCAGC TGGCGTAATA
 481  GCGAAGAGGC CCGCACCGAT CGCCCTTCCC AACAGTTGCG CAGCCTGAAT GGCGAATGGG
 541  ACGCGCCCTG TAGCGGCGCA TTAAGCGCGG CGGGTGTGGT GGTTACGCGC AGCGTGACCG
 601  CTACACTTGC CAGCGCCCTA CCGCCCGCTC CTTTCGCTTT CTTCCCTTCC TTTCTCGCCA
 661  CGTTCGCCGG CTTTCCCCGT CAAGCTCTAA ATCGGGGGCT CCCTTTAGGG TTCCGATTTA
 721  GTGCTTTACG GCACCTCGAC CCCAAAAAAC TTGATTAGGG TGATGGTTCA CGTAGTGGGC
 781  CATCGCCCTG ATAGACGGTT TTTCGCCCTT TGACGTTGGA GTCCACGTTC TTTAATAGTG
 841  GACTCTTGTT CCAAACTGGA ACAACACTCA ACCCTATCTC GGTCTATTCT TTTGATTTAT
 901  AAGGGATTTT GCCGATTTCG GCCTATTGGT TAAAAAATGA GCTGATTTAA CAAAAATTTA
 961  ACGCGAATTT TAACAAAATA TTAACGTTTA CAATTTCAGG TGGCACTTTT CGGGGAAATG
1021  TGCCCGGAAC CCCTATTTGT TTATTTTTCT AAATACATTC AAATATGTAT CCGCTCATGA
1081  GACAATAACC CTGATAAATG CTTCAATAAT ATTGAAAAAG GAAGAGTATG AGTATTCAAC       INITIATION
1141  ATTTCCGTGT CGCCCTTATT CCCTTTTTTG CGGCATTTTG CCTTCCTGTT TTTGCTCACC       CODON OF
1201  CAGAAACGCT GGTGAAACTA AAAGATGCTG AAGATCAGTT GGGTGCACGA GTGGGTTACA       β-LACTAMASE
1261  TCGAACTGGA TCTCAACAGC GGTAAGATCC TTGAGAGTTT TCGCCCCGAA GAACGTTTTC
1321  CAATGATGAG CACTTTTAAA GTTCTGCTAT GTGGCGCGGT ATTATCCCGT ATTGACGCCG
1381  GGCAAGAGCA ACTCGGTCGC CGCATACACT ATTCTCAGAA TGACTTGGTT GAGTACTCAC
1441  CAGTCACAGA AAAGCATCTT ACGGATGGCA TGACAGTAAG AGAATTATGC AGTGCTGCCA
1501  TAACCATGAG TGATAACACT GCGGCCAACT TACTTCTGAC AACGATCGGA GGACCGAAGG
1561  AGCTAACCGC TTTTTTGCAC AACATGGGGG ATCATGTAAC TCGCCTTGAT CGTTGGGAAC
1621  CGGAGCTGAA TGAAGCCATA CCAAACGACG AGCGTGACAC CACGATGCCT GTAGCAATGG
1681  CAACAACGTT GCGCAAACTA TTAACTGGCG AACTACTTAC TCTAGCTTCC CGGCAACAAT
1741  TAATAGACTG GATGGAGGCG GATAAAGTTG CAGGACCACT TCTGCGCTCG GCCCTTCCGG
1801  CTGGCTGGTT TATTGCTGAT AAATCTGGAG CCGGTGAGCG TGGGTCTCGC GGTATCATTG
1861  CAGCACTGGG GCCAGATGGT AAGCCCTCCC GTATCGTAGT TATCTACACG ACGGGGAGTC
1921  AGGCAACTAT GGATGAACGA AATAGACAGA TCGCTGAGAT AGGTGCCTCA CTGATTAAGC
```

*FIG. 4*

```
1981  ATTGGTAACT GTCAGACCAA GTTTACTCAT ATATACTTTA GATTGATTTA AAACTTCATT  STOP CODON
2041  TTTAATTTAA AAGGATCTAG GTGAAGATCC TTTTTGATAA TCTCATGACC AAAATCCCTT      OF
2101  AACGTGAGTT TTCGTTCCAC TGAGCGTCAG ACCCCGTAGA AAAGATCAAA GGATCTTCTT  β-LACTAMASE
2161  GAGATCCTTT TTTTCTGCGC GTAATCTGCT GCTTGCAAAC AAAAAAACCA CCGCTACCAG
2221  CGGTGGTTTG TTTGCCGGAT CAAGAGCTAC CAACTCTTTT TCCGAAGGTA ACTGGCTTCA
2281  GCAGAGCGCA GATACCAAAT ACTGTCCTTC TAGTGTAGCC GTAGTTAGGC CACCACTTCA
2341  AGAACTCTGT AGCACCGCCT ACATACCTCG CTCTGCTAAT CCTGTTACCA GTGGCTGCTG
2401  CCAGTGGCGA TAAGTCGTGT CTTACCGGGT TGGACTCAAG ACGATAGTTA CCGGATAAGG
2461  CGCAGCGGTC GGGCTGAACG GGGGGTTCGT GCACACAGCC CAGCTTGGAG CGAACGACCT
2521  ACACCGAACT GAGATACCTA CAGCGTGAGC ATTGAGAAAG CGCCACGCTT CCCGAAGGGA
2581  GAAAGGCGGA CAGGTATCCG GTAAGCGGCA GGGTCGGAAC AGGAGAGCGC ACGAGGGAGC
2641  TTCCAGGGGG AAACGCCTGG TATCTTTATA GTCCTGTCGG GTTTCGCCAC CTCTGACTTG
2701  AGCGTCGATT TTTGTGATGC TCGTCAGGGG GGCGGAGCCT ATGGAAAAAC GCCAGCAACG
2761  CGGCCTTTTT ACGGTTCCTG GCCTTTTGCT GGCCTTTTGC TCACATGTTC TTTCCTGCGT
2821  TATCCCCTGA TTCTGTGGAT AACCGTATTA CCGCCTTTGA GTGAGCTGAT ACCGCTCGCC
2881  GCAGCCGAAC GACCGAGCGC AGCGAGTCAG TGAGCGAGGA AGCGGAAG
```

*FIG. 5*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 2927 base pairs
      (B) TYPE: nucleic acid
      (C) STRANDEDNESS: single (D) TOPOLOGY: linear (ii) MOLECULE TYPE: DNA (genomic)

(xi) SEQUENCE DESCRIPTION: SEQ ID NO:1:

| | | | | | |
|---|---|---|---|---|---|
| AGCGCCCAAT | ACGCAAACCG | CCTCTCCCCG | CGCGTTGGCC | GATTCATTAA | TGCAGCTGGC | 60 |
| ACGACAGGTT | TCCCGACTGG | AAAGCGGGCA | GTGAGCGCAA | CGCAATTAAT | GTGAGTTAGC | 120 |
| TCACTCATTA | GGCACCCCAG | GCTTTACACT | TTATGCTTCC | GGCTCGTATG | TTGTGTGGAA | 180 |
| TTGTGAGCGG | ATAACAATTT | CACACAGGAA | ACAGCTATGA | CCATGATTAC | GCCAAGCTCT | 240 |
| AATACGACTC | ACTATAGGGA | AGCTTCCCT | GTTGACAATT | AATCATCGAA | CTAGTTAACA | 300 |
| GTACGCAAGT | TCACGTAAAA | AGGGTAGAAT | TCGAGCTCGG | TACCCGGGGA | TCCTCTAGAG | 360 |
| TCGACCTGCA | GGTCGAAATT | CACTGGCCGT | CGTTTTACAA | CGTCGTGACT | GGGAAAACCC | 420 |
| TGGCGTTACC | CAACTTAATC | GCCTTGCAGC | ACATCCCCCT | TTCGCCAGCT | GGCGTAATAG | 480 |
| CGAAGAGGCC | CGCACCGATC | GCCCTTCCCA | ACAGTTGCGC | AGCCTGAATG | GCGAATGGGA | 540 |
| CGCGCCCTGT | AGCGGCGCAT | TAAGCGCGGC | GGGTGTGGTG | GTTACGCGCA | GCGTGACCGC | 600 |
| TACACTTGCC | AGCGCCCTAC | CGCCCGCTCC | TTTCGCTTTC | TTCCCTTCCT | TTCTCGCCAC | 660 |
| GTTCGCCGGC | TTTCCCCGTC | AAGCTCTAAA | TCGGGGCTC | CCTTTAGGGT | TCCGATTTAG | 720 |
| TGCTTTACGG | CACCTCGACC | CCAAAAAACT | TGATTAGGGT | GATGGTTCAC | GTAGTGGGCC | 780 |
| ATCGCCCTGA | TAGACGGTTT | TTCGCCCTTT | GACGTTGGAG | TCCACGTTCT | TTAATAGTGG | 840 |
| ACTCTTGTTC | CAAACTGGAA | CAACACTCAA | CCCTATCTCG | GTCTATTCTT | TTGATTTATA | 900 |
| AGGGATTTTG | CCGATTTCGG | CCTATTGGTT | AAAAAATGAG | CTGATTTAAC | AAAAATTTAA | 960 |
| CGCGAATTTT | AACAAAATAT | TAACGTTTAC | AATTTCAGGT | GGCACTTTTC | GGGGAAATGT | 1020 |
| GCCCGGAACC | CCTATTTGTT | TATTTTTCTA | AATACATTCA | AATATGTATC | CGCTCATGAG | 1080 |
| ACAATAACCC | TGATAAATGC | TTCAATAATA | TTGAAAAAGG | AAGAGTATGA | GTATTCAACA | 1140 |
| TTTCCGTGTC | GCCCTTATTC | CCTTTTTTGC | GGCATTTTGC | CTTCCTGTTT | TTGCTCACCC | 1200 |
| AGAAACGCTG | GTGAAACTAA | AAGATGCTGA | AGATCAGTTG | GGTGCACGAG | TGGGTTACAT | 1260 |
| CGAACTGGAT | CTCAACAGCG | GTAAGATCCT | TGAGAGTTTT | CGCCCCGAAG | AACGTTTTCC | 1320 |
| AATGATGAGC | ACTTTTAAAG | TTCTGCTATG | TGGCGCGGTA | TTATCCCGTA | TTGACGCCGG | 1380 |
| GCAAGAGCAA | CTCGGTCGCC | GCATACACTA | TTCTCAGAAT | GACTTGGTTG | AGTACTCACC | 1440 |
| AGTCACAGAA | AAGCATCTTA | CGGATGGCAT | GACAGTAAGA | GAATTATGCA | GTGCTGCCAT | 1500 |
| AACCATGAGT | GATAACACTG | CGGCCAACTT | ACTTCTGACA | ACGATCGGAG | GACCGAAGGA | 1560 |
| GCTAACCGCT | TTTTTGCACA | ACATGGGGGA | TCATGTAACT | CGCCTTGATC | GTTGGGAACC | 1620 |
| GGAGCTGAAT | GAAGCCATAC | CAAACGACGA | GCGTGACACC | ACGATGCCTG | TAGCAATGGC | 1680 |
| AACAACGTTG | CGCAAACTAT | TAACTGGCGA | ACTACTTACT | CTAGCTTCCC | GGCAACAATT | 1740 |
| AATAGACTGG | ATGGAGGCGG | ATAAAGTTGC | AGGACCACTT | CTGCGCTCGG | CCCTTCCGGC | 1800 |
| TGGCTGGTTT | ATTGCTGATA | AATCTGGAGC | CGGTGAGCGT | GGGTCTCGCG | GTATCATTGC | 1860 |
| AGCACTGGGG | CCAGATGGTA | AGCCCTCCCG | TATCGTAGTT | ATCTACACGA | CGGGGAGTCA | 1920 |
| GGCAACTATG | GATGAACGAA | ATAGACAGAT | CGCTGAGATA | GGTGCCTCAC | TGATTAAGCA | 1980 |
| TTGGTAACTG | TCAGACCAAG | TTTACTCATA | TATACTTTAG | ATTGATTTAA | AACTTCATTT | 2040 |
| TTAATTTAAA | AGGATCTAGG | TGAAGATCCT | TTTTGATAAT | CTCATGACCA | AAATCCCTTA | 2100 |
| ACGTGAGTTT | TCGTTCCACT | GAGCGTCAGA | CCCCGTAGAA | AAGATCAAAG | GATCTTCTTG | 2160 |
| AGATCCTTTT | TTTCTGCGCG | TAATCTGCTG | CTTGCAAACA | AAAAAACCAC | CGCTACCAGC | 2220 |

```
GGTGGTTTGT TTGCCGGATC AAGAGCTACC AACTCTTTTT CCGAAGGTAA CTGGCTTCAG      2280

CAGAGCGCAG ATACCAAATA CTGTCCTTCT AGTGTAGCCG TAGTTAGGCC ACCACTTCAA      2340

GAACTCTGTA GCACCGCCTA CATACCTCGC TCTGCTAATC CTGTTACCAG TGGCTGCTGC      2400

CAGTGGCGAT AAGTCGTGTC TTACCGGGTT GGACTCAAGA CGATAGTTAC CGGATAAGGC      2460

GCAGCGGTCG GGCTGAACGG GGGGTTCGTG CACACAGCCC AGCTTGGAGC GAACGACCTA      2520

CACCGAACTG AGATACCTAC AGCGTGAGCA TTGAGAAAGC GCCACGCTTC CCGAAGGGAG      2580

AAAGGCGGAC AGGTATCCGG TAAGCGGCAG GGTCGGAACA GGAGAGCGCA CGAGGGAGCT      2640

TCCAGGGGGA AACGCCTGGT ATCTTTATAG TCCTGTCGGG TTTCGCCACC TCTGACTTGA      2700

GCGTCGATTT TTGTGATGCT CGTCAGGGGG CGGAGCCTA TGGAAAAACG CCAGCAACGC      2760

GGCCTTTTTA CGGTTCCTGG CCTTTTGCTG GCCTTTTGCT CACATGTTCT TTCCTGCGTT      2820

ATCCCCTGAT TCTGTGGATA ACCGTATTAC CGCCTTTGAG TGAGCTGATA CCGCTCGCCG      2880

CAGCCGAACG ACCGAGCGCA GCGAGTCAGT GAGCGAGGAA GCGGAAG                   2927

(2) INFORMATION FOR SEQ ID NO:2:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GGGAATTCAT GGCATCACGT CGAGGTAATC GATCTCAAGC GGTGAGGCAT GG              52

(2) INFORMATION FOR SEQ ID NO:3:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GGGGATCCTC AGGAGTACTC GAGGGTGAAC TTGGCATGGA AC                        42

(2) INFORMATION FOR SEQ ID NO:4:

(i) SEQUENCE CHARACTERISTICS:
        (A) LENGTH: 1491 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

ATGGCATCAC GTCGAGGTAA TCGATCTCAA GCGGTGAGGC ATGGACTGAG GGCGAAGGTG       60

CTGACGCTGG ACGGCATGAA CCCGCGTGTG CGGAGAGTGG AGTACGCAGT GCGTAGCCCC      120

ATAGTGCAGC GAGCCTTGGA GCTGGAGCAG GAGCTGCGCC AGGGTGTGAA GAAGCCTTTC      180

ACCGAGGTCA TCCGTGCCAA CATCGGGGAC GCACAGGCTA TGGGGCAGAG GCCCATCACC      240

TTCCTGCGTC AGGTCTTGGC CCTCTGTGTT AACCCTGATC TTCTGAGCAG CCCCAACTTC      300

CCTGACGATG CCAAGAAAAG GGCGGAGCGC ATCTTGCAGG CGTGTGGGGG CCACAGTCTG      360

GGGGCCTACA GCGTCAGCTC CGGCATCCAG CTGATCCGGG AGGACGTGGC GCGGTACATT      420
```

-continued

```
GAGAGGCGTG ACGGAGGCAT CCCTGCGGAC CCCAACAACG TCTTCCTGTC CACAGGGGCC    480

AGCGATGCCA TCGTGACGGT GCTGAAGCTG CTGGTGGCCG GCGAGGGCCA CACACGCACG    540

GGTGTGCTCA TCCCCATCCC CCAGTACCCA CTCTACTCGG CCACGCTGGC AGAGCTGGGC    600

GCAGTGCAGG TGGATTACTA CCTGGACGAG GAGCGTGCCT GGGCGCTGGA CGTGGCCGAG    660

CTTCACCGTG CACTGGGCCA GGCGCGTGAC CACTGCCGCC CTCGTGCGCT CTGTGTCATC    720

AACCCTGGCA ACCCCACCGG GCAGGTGCAG ACCCGCGAGT GCATCGAGGC CGTGATCCGC    780

TTCGCCTTCG AAGAGCGGCT CTTTCTGCTG GCGGACGAGG TGTACCAGGA CAACGTGTAC    840

GCCGCGGGTT CGCAGTTCCA CTCATTCAAG AAGGTGCTCA TGGAGATGGG GCCGCCCTAC    900

GCCGGGCAGC AGGAGCTTGC CTCCTTCCAC TCCACCTCCA AGGGCTACAT GGGCGAGTGC    960

GGGTTCCGCG GCGGCTATGT GGAGGTGGTG AACATGGACG CTGCAGTGCA GCAGCAGATG   1020

CTGAAGCTGA TGAGTGTGCG GCTGTGCCCG CCGGTGCCAG GACAGGCCCT GCTGGACCTG   1080

GTGGTCAGCC CGCCCGCGCC CACCGACCCC TCCTTTGCGC AGTTCCAGGC TGAGAAGCAG   1140

GCAGTGCTGG CAGAGCTGGC GGCCAAGGCC AAGCTCACCG AGCAGGTCTT CAATGAGGCT   1200

CCTGGCATCA GCTGCAACCC AGTGCAGGGC GCCATGTACT CCTTCCCGCG CGTGCAGCTG   1260

CCCCCGCGGG CGGTGGAGCG CGCTCAGGAG CTGGGCCTGG CCCCCGATAT GTTCTTCTGC   1320

CTGCGCCTCC TGGAGGAGAC CGGCATCTGC GTGGTGCCAG GGAGCGGCTT TGGGCAGCGG   1380

GAAGGCACCT ACCACTTCCG GATGACCATT CTGCCCCCCT TGGAGAAACT GCGGCTGCTG   1440

CTGGAGAAGC TGAGCAGGTT CCATGCCAAG TTCACCCTCG AGTACTCCTG A            1491
```

METHOD FOR PRODUCING ACTIVE HUMAN ALANINE AMINOTRANSFERASE

This application is a continuation of U.S. application Ser. No. 08/533,717 filed on Sep. 26, 1995, now abandoned.

DETAILED DESCRIPTION OF THE INVENTION

1. Field of the Invention:

The present invention relates to production of human ALT (alanine aminotransferase), especially to production of human ALT with sufficient enzymatic activity.

More precisely, the present invention relates to a novel plasmid having a mutated human ALT gene, in which the DNA sequence encoding the N-terminal region of human ALT has been mutated without causing amino acid substitution while, at the same time, restriction endonuclease sites have been added to the upstream and downstream sites of the gene, and also to *Escherichia coli* that has been transformed with this plasmid as well as a method for production of human ALT as an active enzyme in the *Escherichia coli* transformant.

2. Prior Art:

Human ALT is an enzyme that is leaked into the serum of a patient suffering from hepatic diseases such as viral hepatitis, hepatocirrhosis, etc., and is important as a clinical marker. The standardization for determination of ALT activity is one of important themes in the serodiagnosis for human ALT. At present, partially purified preparation from porcine heart is used as the standard enzyme. However, this is different from the human enzyme in catalytic properties such as substrate specificity, Km value, etc. Therefore, it has been desired to produce the human enzyme, ALT as an active form.

On the other hand, recently, it has become possible to produce heterologous proteins by using microorganisms by means of gene engineering technology, and such has been put to practical use. For instance, it is described in Science, 198, 1056, 1978 that an animal protein was produced in *Escherichia coli* carrying a plasmid modified by introducing a lactose promoter into plasmid pBR322. In the case of human ALT, its gene has been cloned and the expression of the gene in *Escherichia coli* has been attempted. However, there is no report relative to the expression of the ALT with a sufficient activity.

PROBLEMS TO BE SOLVED BY THE INVENTION

The standarization for determination of the ALT activity is one of important themes in the field of clinical examination. At present, partially purified ALT from porcine heart is used as the standard enzyme for this purpose. However, this is different from the human enzyme in catalytic properties such as substrate specificity, Km value, etc. Therefore, it is desired to utilize an active human ALT. However, it was difficult to prepare industrially a large amount of the enzyme from human tissue.

BRIEF DESCRIPTION OF THE DRAWINGS

FIG. 4 shows residues 1–1320 of the full-length DNA sequence of the expression vector pTRP (SEQ. ID. NO: 1).

FIG. 5 shows residues 1321–1491 of the full-length DNA sequence of the expression vector pTRP (SEQ. ID. NO: 1 ).

MEANS FOR SOLVING THE PROBLEMS

Figure 1:
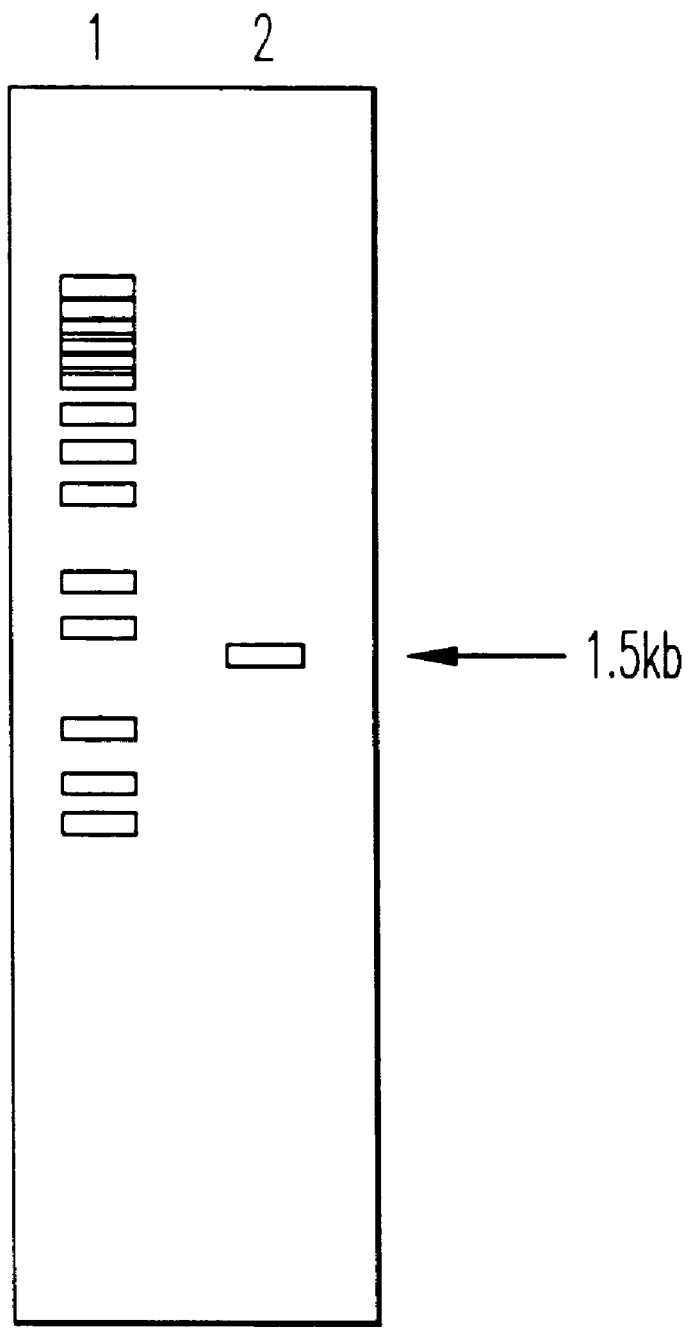
FIG. 1 shows a pattern of agarose gel electrophoresis of a PCR-amplified product corresponding to the mutated human ALT. PCR was performed, using the sense primer and the anti-sense primer shown in Example 1 and using plasmid pHGT-39 having a cloned, human liver-ALT gene as a template. The lane 1 indicates a 1 kb DNA ladder (produced by GIBCO BRL Co.), and the lane 2 indicates the PCR-amplified product.

We, the present inventors have developped a mutated human ALT gene, in which the DNA sequence encoding the N-terminal region of human ALT has been mutated without causing amino acid substitution while, at the same time, restriction endonuclease sites have been added to the upstream and downstream sites of the gene, and also a recombinant plasmid to be constructed by insertion of the mutated human ALT gene to a vector plasmid, *Esherichia coli* that has been transformed with the recombinant plasmid, and a method for production of human ALT as an active enzyme in the transformant. First, a mutated human ALT gene, in which the DNA sequence corresponding to the N-terminal region of human ALT has been mutated without causing amino acid substitution while, at the same time, restriction endonuclease sites have been added to the upstream and downstream sites of the gene, has been amplified by PCR (polymerase chain reaction), using a plasmid containing a cloned, human ALT gene as a template. After a plasmid carrying the mutated human ALT gene was obtained, *Escherichia coli* was transformed with the recombinant plasmid to create a *Escherichia coli* transformant. The *Escherichia coli* transformant has been cultivated to exhibit actual expression of human ALT as an active enzyme. Thus, the present invention has been completed.

Specifically, the gist of the present invention resides in a recombinant plasmid including a PCR-mutated human ALT gene, in which the DNA sequence encoding the N-terminal region of human ALT has been mutated without causing amino acid substitution while, at the same time, restriction endonuclease sites have been added to the upstream and downstream sites of the gene, followed by insertion of the thus-amplified gene into a vector plasmid, and also in *Escherichia coli* that has been transformed with the recombinant plasmid having the PCR-mutated human ALT gene, in which the DNA sequence encoding the N-terminal region of human ALT has been mutated without causing amino acid substitution while, at the same time, restriction endonuclease sites have been added to the upstream and downstream sites of the gene, followed by insertion of the thus-amplified gene into a vector plasmid.

To obtain the plasmid of the present invention, for example, a human ALT gene, a promoter, and a DNA that functions as a vector are digested with restriction enzymes according to the method described in J. Mol. Biol., 96, 171–184, 1974, and then ligated with a ligase according to the method described in Biochem. Biophys. Acta, 72, 619–629, 1963.

The DNA functioning as a vector includes, for example, *Escherichia coli* pBR322, etc. The promoter includes, for example, tac promoter, tryptophan promoter, lambda PL promoter, lambda PR promoter, lactose promoter, T7 promoter, etc. The restriction enzyme includes, for example, EcoRI and BamHI. The ligase includes, for example, T4 DNA ligase.

The mutated human ALT gene in the present invention can be amplified by PCR, using a cloned, human liver ALT gene as a template. The sense primer (SEQ. ID. NO: 2) is a synthetic oligodeoxy-nucleotide that has been designed on the basis of the DNA sequence of human ALT gene by partly changing the codon without causing amino acid substitution to mutate the DNA sequence encoding the N-terminal region of human ALT. On the other hand, the anti-sense primer (SEQ. ID. No: 3) is a synthetic oligo-nucleotide that has been designed on the basis of the DNA sequence corresponding to the C-terminal region of human ALT. Introduction of the mutated human ALT gene into an expression vector PTRP can construct recombinant plasmid pTRAL-112 to produce human ALT in *Escherichia coli* cytosol. Transformation of the recombinant plasmid, having the mutated human ALT gene of the present invention, into *Escherichia coli* fields a transformant which produces human ALT in the cytosol.

Figure 2:
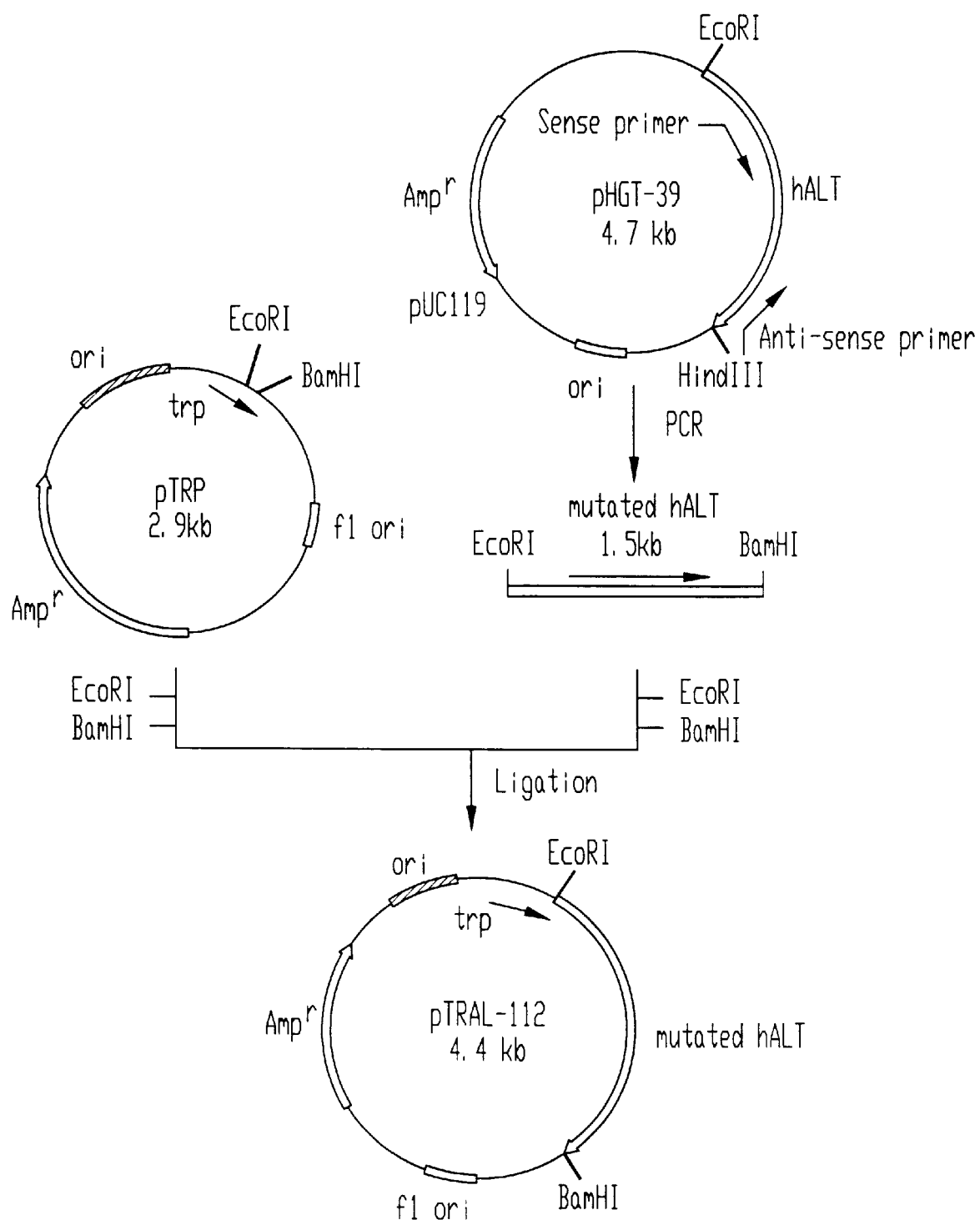
FIG. 2 shows the construction of *Escherichia coli* recombinant plasmid pTRAL-112 having the PCR-mutated human ALT gene.

The cloned, human liver ALT gene above-mentioned is, for example, referred to as plasmid pHGT-39 (FIG. 2). The sense primer and the anti-sense primer mentioned above are, for example, referred to as the following sequences.

Sense Primer (SEQ ID NO:2)

5'-GG<u>GAATTC</u>ATGGCATCACG<u>TC</u>GAGGTAA<u>TC</u>G<u>ATCT</u>CA<u>A</u>GCGGTGAGGCATGG-3'

<u>E c o R I</u>

Anti-sense Primer (SEQ ID NO:3)

5'-GG<u>GGATCC</u>TCAGGAGTACTCGAGGGTGAACTTGGCATGGAAC-3'
<u>B a m H I</u>

It is possible to produce a large amount of huamn ALT, especially human ALT with a sufficient enzymatic activity, by cultivation of the *Escherichia coli* transformant constructed in the manner above-mentioned, in a suitable medium. Isolation of the human ALT from the culture may be, for example, achieved by disruption of the cells with sonication, etc. and then by the separation.

Not only the host-vector system of *Escherichia coli* above-mentioned but also other host-vector systems of *Bacillus subtilis*, yeast, Chinese hamster ovary cells (CHO cells), etc. can be utilized in the present invention. Using any of these systems, mass-production of human ALT is possible according to the present invention.

EXAMPLES

Next, the present invention is described more concretely by means of the following Example.

Example 1

(a) Amplification of mutated human ALT gene by PCR:

A mutated human ALT gene was amplified, using plasmid pHGT-39 having a cloned, human liver ALT gene as a template and using the following sense primer and anti-sense primer.

Sense Primer (SEQ ID NO:2)

5'-GG<u>GAATTC</u>ATGGCATCACG<u>TC</u>GAGGTAA<u>TC</u>G<u>ATCT</u>CA<u>A</u>GCGGTGAGGCATGG-3'

<u>E c o R I</u>

Anti-sense Primer (SEQ ID NO:3)

5'-GG<u>GGATCC</u>TCAGGAGTACTCGAGGGTGAACTTGGCATGGAAC-3'
<u>B a m H I</u>

The DNA sequence of the sense primer was designed on the basis of the sequence encoding the N-terminal region of human ALT by partly exchanging the codon without causing amino acid substitution. The DNA sequence of the anti-sense primer was designed on the basis of the sequence encoding the C-terminal region of human ALT. Restriction endonuclease sites for EcoRI and BamHI were added to the 5'-end of the two primers, respectively. The underlines in the above-mentioned primers indicate the bases exchanged and the restriction endonuclease sites added. The reaction mixture (total 100 µl) used for PCR-amplification of the mutated human ALT gene was comprised of 50 mM KCl, 10 mM Tris-HCl (pH 8.3), 1.5 mM $MgCl_2$, 0.01% (W/V) gelatin, 100 µM each dNTP, 0.5 µM each the primers, 40 pg of a plasmid (pHGT-39) having a cloned human ALT gene, and 2.5 U of Taq polymerase (produced by PERKIN ELMER CETUS Co.). After it was prepared, the mixture was overlaid with 100 µl of a mineral oil.

On the reaction conditions for PCR, the denaturation step was performed at 94° C. for one minute, the annealing step was at 55° C. for one minute and the polymerase reaction step was at 72° C. for 1 minute and 15 seconds. 35 cycles of the incubation comprising these steps as one cycle were conducted.

After the reaction mixture was extracted with phenol to remove protein impurities, a DNA fraction containing the PCR-amplified product was recovered by precipitation with cold ethanol. The product thus-obtained was subjected to agarose gel electrophoresis to confirm the amplification of the mutated human ALT gene of about 1.5 kb (FIG. 1).

(b) Preparation of recombinant plasmid pTRAL for expression of human ALT:

pTRP was used as the expression vector. The vector is about 2.9 kb length, and carries a tryptophan promoter, a Shine-Delgaino sequence (SD sequence) and a multi-cloning site for EcoRI and BamHI. Restriction enzymes EcoRI (produced by GIBCO BRL Co.) and BamHI (produced by GIBCO BRL Co.) were added to each 1 μg of this pTRP and 2 μg of the mutated human ALT gene fragment amplified in the above-mentioned step (a), and these were reacted in 100 μl of a 50 mM Tris-buffer (pH 7.2) containing 10 mM of $MgCl_2$ and 0.1 mM of NaCl at 37° C. for 2 hours. These reaction mixtures each were subjected to agarose gel electrophoresis, and an EcoRI-BamHI fragments with 2.9 kb and 1.5 kb, respectively, were extracted from the agarose gels, using Glagg Max TM DNA Isolation Spin Cartridge System (produced by GIBCO BRL Co.).

Figure 3:
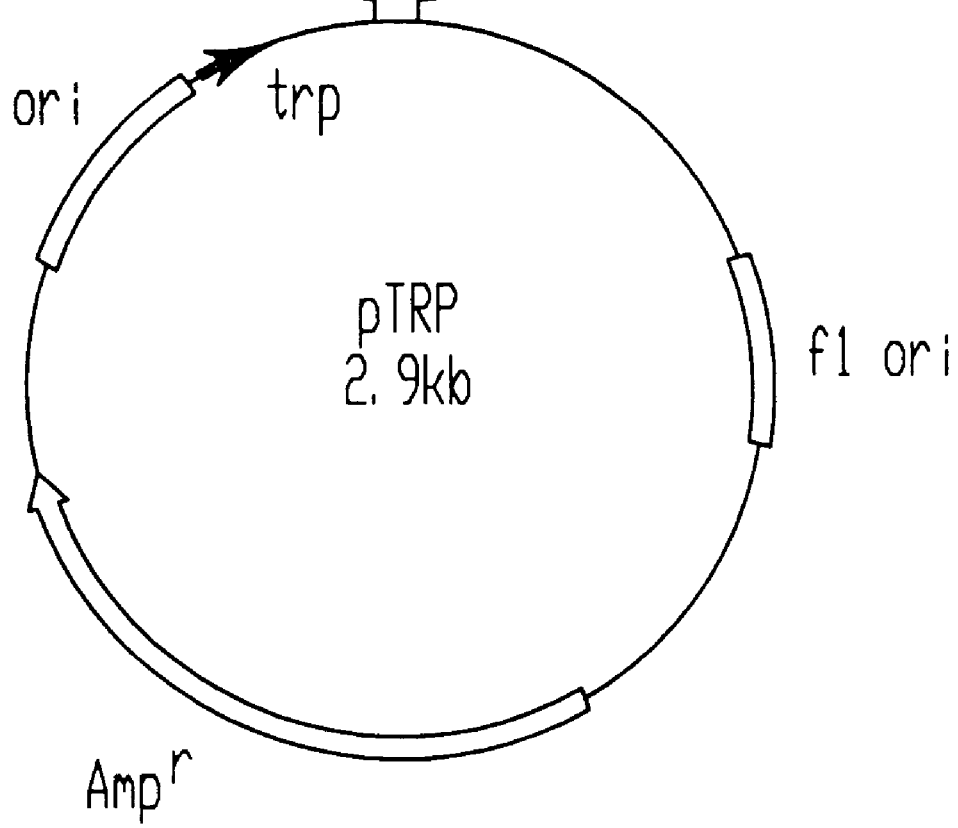
FIG. 3 shows an expression vector pTRP.

Next, 10 ng of the about 1.5 kb mutated human ALT gene digested with EcoRI-BamHI was ligated to 10 ng of the about 2.9 kb pTRP digested with EcoRI-BamHI, using a DNA ligation kit (produced by Takara Shuzo KK) to give recombinant plasmid pTRAL-112. *Escherichia coli* JM101 strain was transformed with this reaction mixture according to a TSS (transformation storage solution) method (Proc. Natl. Acad. Sci., USA, *86, 2172–2175, 1989*). The ampicillin-resistant transformants that had grown on an LB agar plate containing 50 μg/ml of ampicillin (prepared by dissolving 10 g of trypton (produced by Difco Co.), yeast extract (produced by Difco Co.), 5 g of NaCl and 15 g of agar powder in one liter of distilled water, and adjusted to pH 7.4) were cultivated on LB medium. After plasmid DNA was extracted from the culture according to Bimboim, Doly, et al's method (Nucleic Acids Res., 7, 1513–1523, 1979), it was digested with EcoRI and BamHI and subjected to agarose gel electrophoresis to confirm the correct insertion of the 1.5 kb-mutated human ALT gene into the expression vector pTRP. FIG. 2 shows the process of constructing the recombinant plasmid pTRAL-112. FIG. 3 shows the structure of the expression vector pTRP. FIG. 4 and FIG. 5 show the full-length DNA sequence of the expression vector pTRP (SEQ ID. NO: 1).

(c) Expression of recombinant active human ALT in *Escherichia coli*:

The recombinant plasmid pTRAL-112 that had been prepared in the above-mentioned step (b) was introduced into *Escherichia coli* JM101 strain according to the TSS method, and the human ALT expressed in the resulting *Escherichia coli* transformant JM101(pTRAL-112) was analyzed in the manner mentioned below. The transformant obtained was referred to as *Escherichia coli* JM101/pTRAL-112 and was subjected to international deposition in the National Institute of Bioscience and Human-Technology of the Agency of Industrial Science and Technology in Japan under FERM BP-4818.

The *Escherichia coli* transformant JM101(pTRAL-112) (FERM BP-4818) was inoculated into 200 ml of LB medium and cultivated at 30° C. After reached the late-logarithmic growth phase in 18 hours, the culture was transferred into 14 liters of the same medium. The transformant was cultivated on the LB medium in the same manner at 30° C. After thus cultured for 18 hours, the cells reached the late-logarithmic growth phase and these were harvested by centrifugation (10,000×g, 10 minutes). The harvested wet cells were suspended in a pottasium phosphate buffer (50 mM, pH 6.5) of 3-fold weight of the weight of the wet cells. The cells in the suspension were disrupted by sonication and then subjected to centrifugation (10,000×g, 10 minutes) to obtain a cell-free extract.

The ALT activity in the cell-free extract was measured to be 0.174 U/mg-protein. On the other hand, the ALT activity with the host *Escherichia coli* JM101 strain was not detected. These results confirmed that the ALT activity with the transformant JM101(pTRAL-112) is derived from the recombinant human ALT. To 10 μl of the cell-free extract, added was a sample-treating buffer (comprising 50 mM of Tris-HCl (pH 6.8), 6% of SDS, 20% of glycerol, 200 mM of dithiothreitol and 3 mM of phenylmethanesulfonylfluoride (PMSF)) of two-fold volume of the extract, and this was heat-treated at 60° C for 30 minutes and then subjected to SDS-polyacrylamide gel electrophoresis according to a Laemmli et al's method (Nature, 227, 680–685, 1970). After the electrophoresis, the gel was stained with Coomassie Brilliant Blue R-250. As a result, a band of human ALT having a molecular weight of about 55 k was detected. This protein band exhibited a specific cross-reaction with an anti-human ALT antibody. Accordingly, it has been confirmed that the *Escherichia coli* recombinant JM101 (pTRAL-112) efficiently expressed the recombinant human ALT as an active enzyme.

ADVANTAGES OF THE INVENTION

The recombinant plasmid of the present invention comprises a mutated human ALT gene in which the DNA sequence encoding the N-terminal region of human ALT is mutated by PCR. Introduction of the plasmid into *Escherichia coli* is possible to express efficiently a recombinant human ALT as an active enzyme in the cytosol under the control of tryptophan promoter. The thus-obtained recombinant human ALT is the equivalent to the natural human liver ALT. After purified, the recombinant human ALT can be utilized as a standard product in serodiagnosis for correctly measuring the amount of ALT leaked to the serum of a patient suffering from a hepatic disease.

What is claimed is:

1. A mutated human ALT (alanine aminotransferase) gene prepared by PCR (polymerase chain reaction) using:
   another human ALT gene as a template or a plasmid containing the other human ALT gene as a template; and
   a sense primer and an antisense primer, wherein the sense primer comprises the sequence of SEQ ID NO:2 and the antisense primer comprises the sequence of SEQ ID NO:3,
   wherein the protein encoded by the mutated human ALT gene and the protein encoded by the other human ALT gene have identical amino acid sequences.

2. The mutated human ALT gene of claim 1, wherein the plasmid is pHGT-39.

3. A recombinant plasmid constructed by ligating the mutated human ALT gene of claim 1 to a vector plasmid.

4. The recombinant plasmid of claim 3, wherein the vector plasmid is pTRP.

5. The recombinant plasmid of claim 4, wherein the recombinant plasmid is pTRAL-112.

6. *Escherichia coli* transformed with the recombinant plasmid of claim 3.

7. *Escherichia coli* JM101/pTRAL-112 having Accession No. FERM BP-4818.

8. A method for recovery of human ALT protein comprising the steps of:
   cultivating *Escherichia coli* JM101/pTRAL-112 having Accession No. FERM BP-4818, wherein the cultivated *Escherichia coli* produces the human ALT protein; and
   recovering the human ALT protein.

9. An isolated DNA sequence comprising the sequence of SEQ ID NO:4.

* * * * *

UNITED STATES PATENT AND TRADEMARK OFFICE
CERTIFICATE OF CORRECTION

PATENT NO. : 5,952,211

DATED : September 14, 1999

INVENTOR(S): Atsuo NAKAMURA, et al.

It is certified that an error appears in the above-identified patent and that said Letters Patent is hereby corrected as shown below:

On the title page, item [73] has been omitted. It should be:

--[73] Assignee: Oriental Yeast Co., Ltd., Tokyo, Japan--

On the title page, the Firm's information has been omitted. It should be:

--*Attorney, Agent, or Firm*—Oblon, Spivak, McClelland, Maier & Neustadt, P.C.--

Signed and Sealed this

Twenty-second Day of August, 2000

Attest:

Q. TODD DICKINSON

*Attesting Officer*   *Director of Patents and Trademarks*